United States Patent
Thompson, Jr. et al.

(10) Patent No.: US 9,867,896 B2
(45) Date of Patent: Jan. 16, 2018

(54) FRAGRANCE DELIVERY SYSTEM

(71) Applicant: Caffco International Ltd., Montgomery, AL (US)

(72) Inventors: James Lamar Thompson, Jr., Montgomery, AL (US); Wu Jingqing, Huizhou (CN)

(73) Assignee: Caffco International Ltd., Montgomery, AL (US)

( * ) Notice: Subject to any disclaimer, the term of this patent is extended or adjusted under 35 U.S.C. 154(b) by 180 days.

(21) Appl. No.: 14/690,145

(22) Filed: Apr. 17, 2015

(65) Prior Publication Data

US 2015/0297774 A1    Oct. 22, 2015

Related U.S. Application Data

(60) Provisional application No. 61/981,013, filed on Apr. 17, 2014, provisional application No. 61/981,369, (Continued)

(51) Int. Cl.
*A61L 9/04* (2006.01)
*A61L 9/12* (2006.01)
(Continued)

(52) U.S. Cl.
CPC ............ *A61L 9/122* (2013.01); *A61L 2/00* (2013.01); *A61L 9/00* (2013.01); *A61L 9/12* (2013.01)

(58) Field of Classification Search
CPC ................... A61L 9/04; A61L 9/015
See application file for complete search history.

(56) References Cited

U.S. PATENT DOCUMENTS

| 4,059,422 A | 11/1977 | Steiner |
| 4,666,638 A | 5/1987 | Baker et al. |

(Continued)

FOREIGN PATENT DOCUMENTS

| CN | 203489149 U | 3/2014 |
| EP | 0925717 A1 | 6/1999 |

(Continued)

OTHER PUBLICATIONS

Scent Fan product in US market, Scent Savvy Scentique & Scent-in, published Jan. 7, 2011, http://www.samsclub.com/sams/fragrancers/prod11140158.ip; http://www.bescentssavvy.com/onlinestorefragrancers.html, 2 pages.

(Continued)

*Primary Examiner* — Sean E Conley
(74) *Attorney, Agent, or Firm* — Kilpatrick Townsend & Stockton LLP

(57) ABSTRACT

This application generally relates to systems, devices, and methods for delivering a fragrance. In some embodiments, portable fragrance delivery systems are provided. In further embodiments, improved fragrance delivery systems are provided that provide increased dispersion of scented agents. In some embodiments, a fragrance delivery system does not include a light source. Optionally, the fragrance delivery system does not include a heater. A portable power source (e.g., disposable or rechargeable batteries) may be provided to power a fan. The fan may blow air through channels of a fragrance carrier to disperse the vaporizing agent and/or scent released by the fragrance carrier.

16 Claims, 19 Drawing Sheets

Related U.S. Application Data filed on Apr. 18, 2014, provisional application No. 62/016,160, filed on Jun. 24, 2014.

(51) Int. Cl.
*A61L 2/00* (2006.01)
*A61L 9/00* (2006.01)

(56) References Cited

U.S. PATENT DOCUMENTS

| | | | |
|---|---|---|---|
| 4,707,338 A * | 11/1987 | Spector | A61L 9/122 239/54 |
| 4,808,347 A | 2/1989 | Dawn et al. | |
| 5,192,342 A | 3/1993 | Baron et al. | |
| 5,230,867 A | 7/1993 | Kunze et al. | |
| 5,376,338 A | 12/1994 | Zlotnik | |
| 5,431,885 A | 7/1995 | Zlotnik et al. | |
| 5,460,787 A | 10/1995 | Colon | |
| 5,498,397 A | 3/1996 | Horng | |
| 5,547,616 A | 8/1996 | Dancs et al. | |
| 5,565,148 A | 10/1996 | Pendergrass, Jr. | |
| 7,223,166 B1 | 5/2007 | Wiseman, Sr. et al. | |
| 7,942,388 B2 | 5/2011 | Suissa et al. | |
| 8,137,629 B2 | 3/2012 | Faber et al. | |
| 8,158,066 B2 | 4/2012 | Yang et al. | |
| 8,412,029 B2 | 4/2013 | Browder et al. | |
| 8,724,975 B2 | 5/2014 | Browder et al. | |
| 2003/0035729 A1 * | 2/2003 | Chen | F04D 29/263 417/14 |
| 2003/0086815 A1 | 5/2003 | Wesley | |
| 2007/0025888 A1 | 2/2007 | Gupte et al. | |
| 2007/0207066 A1 | 9/2007 | Thur et al. | |
| 2008/0130266 A1 | 6/2008 | DeWitt et al. | |
| 2009/0200393 A1 | 8/2009 | Avelar | |
| 2010/0001417 A1 | 1/2010 | D'Amico | |
| 2010/0044468 A1 | 2/2010 | Granger et al. | |
| 2011/0027124 A1 | 2/2011 | Albee et al. | |
| 2012/0183280 A1 | 7/2012 | Kowalec et al. | |
| 2013/0049236 A1 | 2/2013 | Garon et al. | |

FOREIGN PATENT DOCUMENTS

| | | |
|---|---|---|
| EP | 0962139 A1 | 12/1999 |
| EP | 2287089 A1 | 2/2011 |
| JP | 11216335 A | 8/1999 |
| WO | 1995010352 A1 | 4/1995 |
| WO | 2012093246 A1 | 7/2012 |

OTHER PUBLICATIONS

PCT/US2015/026490, "International Preliminary Report on Patentability", Oct. 27, 2016, 13 pages.

International Patent Application No. PCT/US2015/026490, International Search Report and Written Opinion, dated Jun. 25, 2015, 17 pages.

* cited by examiner

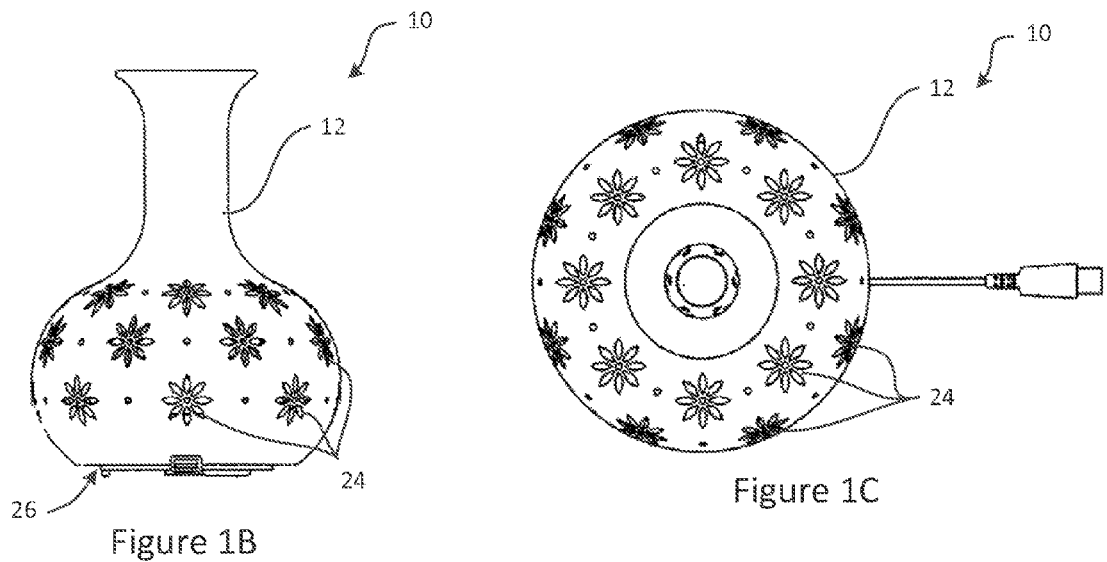
Figure 1B
Figure 1C
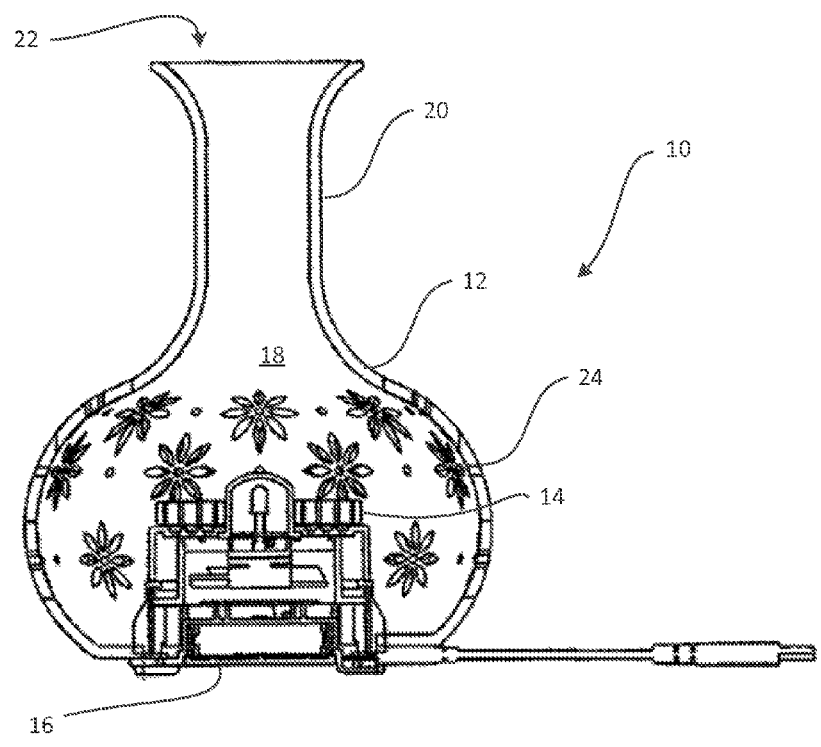
Figure 1D

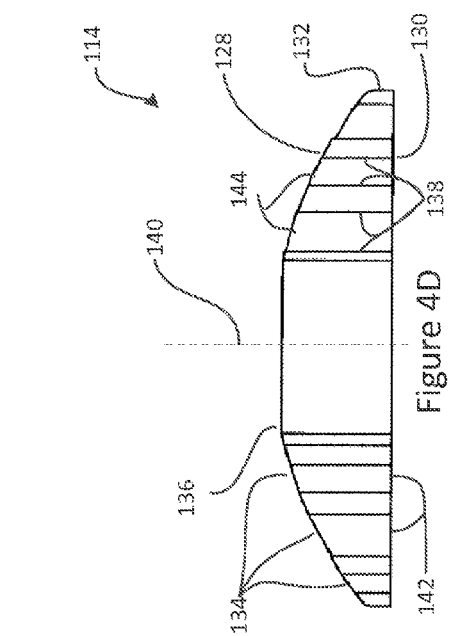
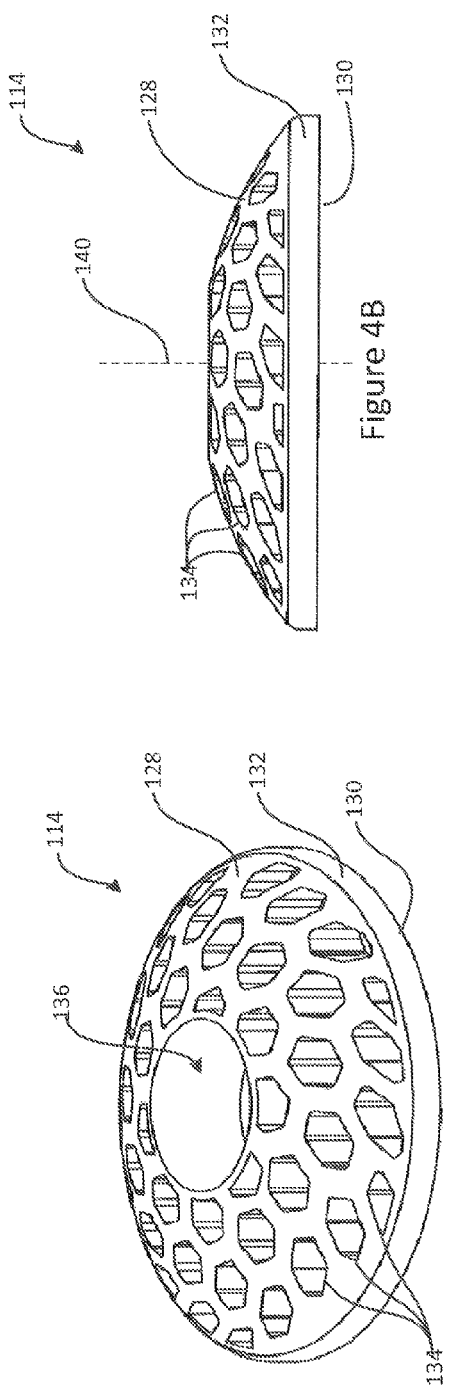
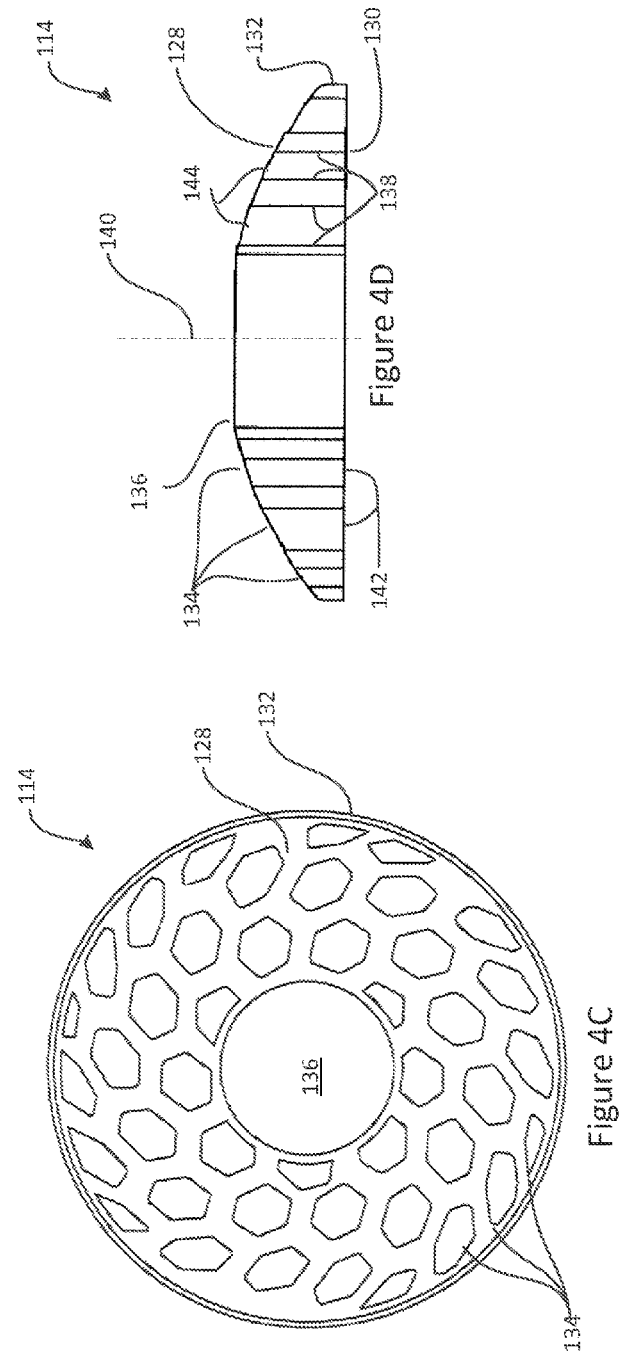

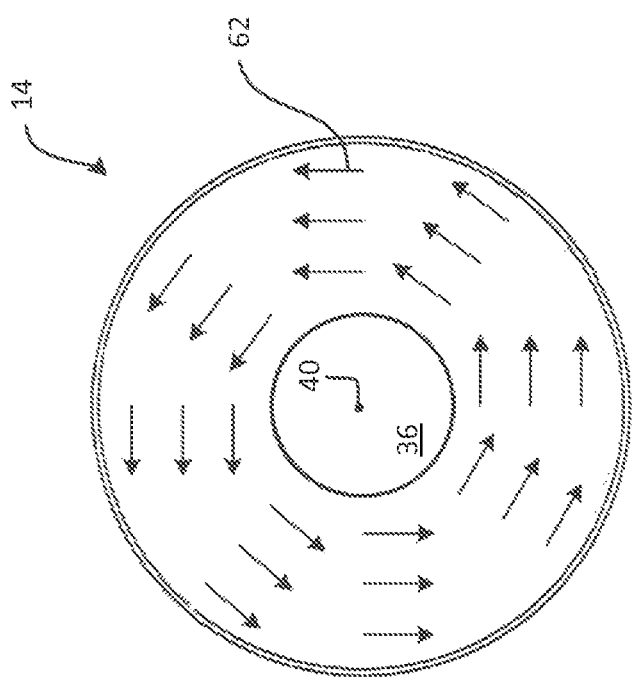
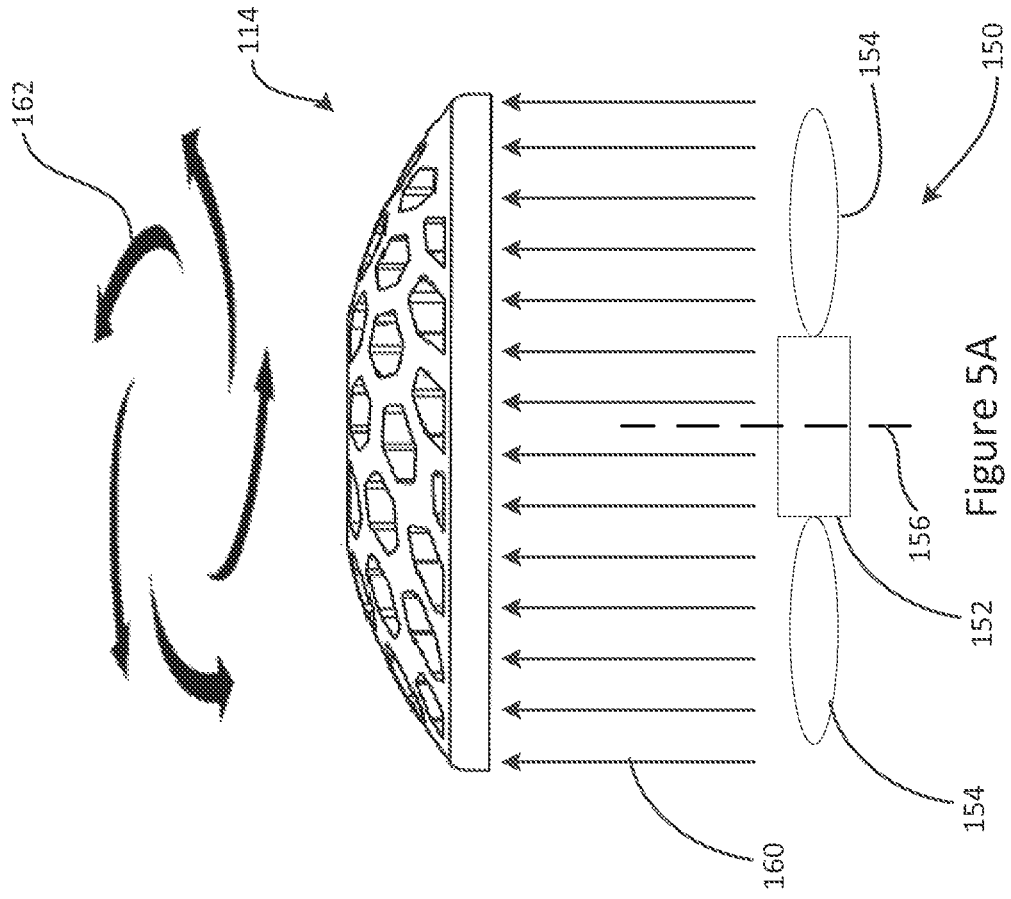
Figure 5A
Figure 5B

FRAGRANCE DELIVERY SYSTEM

CROSS-REFERENCE TO RELATED APPLICATIONS

This application claims priority to and the benefit of U.S. Provisional Patent Application No. 61/981,013 filed on Apr. 17, 2014; U.S. Provisional Patent Application No. 61/981,369 filed on Apr. 18, 2014; and U.S. Provisional Patent Application No. 62/016,160 filed Jun. 24, 2014, the full disclosures of which are incorporated herein by reference in their entirety for all purposes.

BACKGROUND

This application relates generally to systems, devices, and methods for delivering and dispersing a fragrance. In some embodiments, portable fragrance delivery systems are provided. In further embodiments, improved fragrance delivery systems are provided that increase the dispersion of the fragrance.

Various configurations of fragrance devices have been developed. Typically, such devices use various heat sources, such as a tea light or a heat-producing light bulb, that simultaneously act to emit light and also act to slowly warm wax-based substances that are heavily scented with a fragrance. The heat sources of such devices act to turn the waxy fragrance-scented substance from an initial solid state over time into a liquid state. As the wax-based substance warms up, agents within the substance may be dispersed into the air to spread the scent of the fragrance device.

While prior fragrance systems, devices, and methods have been generally sufficient in dispersing scented agents, further improvements may be desired.

BRIEF SUMMARY

In some aspects of the present invention, portable fragrance delivery systems may be provided. The portable fragrance delivery system may include a fan configured to rotate about a fan axis to propel air in a downstream direction from the fan. A partition may be disposed downstream from the fan. The partition may define a first surface facing the fan, a second surface opposite the first surface of the partition, and openings extending from the first surface of the partition to the second surface of the partition. The openings of the partition may be configured to allow air propelled by the fan to travel through the partition and to exit from the second surface of the partition in the downstream direction. A fragrance carrier may be supported by the second surface of the partition and may be configured to emit a scent from surfaces of the fragrance carrier. The fragrance carrier may include a first surface supported by the second surface of the partition and a second surface opposite the first surface of the fragrance carrier. The fragrance carrier may further define a plurality of openings extending from the first surface of the fragrance carrier to the second surface of the fragrance carrier. Each of the plurality of openings may be defined by side walls of the fragrance carrier that extend from the first surface of the fragrance carrier to the second surface of the fragrance carrier. At least some of the openings of the partition may be aligned with at least some of the plurality of openings of the fragrance carrier such that at least a portion of air propelled by the fan that travels through the partition and exits from the second surface of the partition will flow through at least some of the openings of the fragrance carrier to propel the scent emitted from the side walls of the fragrance carrier outwardly in the downstream direction from the second side of the fragrance carrier. In some embodiments, the portable fragrance delivery system may not include a heat source for heating the fragrance carrier. Additionally, in some embodiments, the portable fragrance delivery system may not include a light source.

Optionally, the portable fragrance delivery system may include a portable battery. In some embodiments, the portable battery only powers the fan and no other electrical component. In some embodiments, the portable fragrance delivery system may not include a power cord.

The partition may include a plurality of spaced apart annular rings coupled with one another by legs extending between the plurality of spaced apart annular rings.

In some embodiments, air propelled by the fan through the partition and exiting from the second surface of the partition may flow in an axial direction in the downstream direction. The side walls of the plurality of openings of the fragrance carrier may be configured redirect the axial air flowing therethrough. Some or all of the side walls of the plurality of openings of the fragrance carrier may be at an angle relative to the fan axis so as to redirect the axial air flowing therethrough. Optionally, the side walls of the plurality of openings of the fragrance carrier may be configured to impart a centrifugal air flow on the air flowing therethrough. The centrifugal air flow may increase a dispersion of the scent.

In further aspects, additional fragrance delivery systems may be provided. The fragrance delivery system may include a fan configured to rotate about a fan axis to draw air from an inlet in the upstream direction from the fan and to propel air in a downstream direction from the fan along a flow path of the fan. A partition having a central opening may be disposed downstream from the fan. The partition may have a first surface facing the fan, a second surface opposite the first surface of the partition, and a plurality of vents defining the outlet of the fan flow path that extend from the first surface of the partition to the second surface of the partition. The plurality of vents of the partition may be positioned about the central opening of the partition and may be configured to allow air propelled by the fan to travel through the partition and to exit from the second surface of the partition in the downstream direction. A central protrusion may project from the central opening of the partition in a downstream direction. The central protrusion may have an engagement surface for releasably engaging with a fragrance carrier. A base housing may be disposed upstream of the fan. The base housing may have a first surface facing the fan, a second surface opposite the first surface of the base housing, and a plurality of vents defining the inlet of the fan flow path that extends from the second surface of the base housing to the first surface of the base housing. The plurality of vents of the base housing may be configured to allow air to be drawn to travel through the base housing toward the fan.

The central protrusion may have an outer surface with a width that increases toward a base of the central protrusion. The outer surface of the central protrusion may be configured to friction fit with a fragrance carrier. In some embodiments, the central protrusion may have a frustoconical configuration. In some embodiments, the central protrusion may comprise a transparent light source housing.

A fragrance carrier may be positioned downstream from the fan along the flow path of the fan and configured to emit a scent from surfaces of the fragrance carrier. The fragrance carrier may include a first surface and a second surface opposite the first surface of the fragrance carrier. The fragrance carrier may further define a plurality of channels extending from the first surface of the fragrance carrier to the second surface of the fragrance carrier—each of the plurality of channels having side walls of the fragrance carrier that extend from the first surface of the fragrance carrier to the second surface of the fragrance carrier. The plurality of channels may have an upstream opening at the first surface of the fragrance carrier configured to receive air propelled by the fan along the flow path of the fan and a downstream opening at the second surface of the fragrance carrier. The channels of the fragrance carrier may be configured to impart a centrifugal flow on the air propelled by the fan as the propelled air flows from the upstream opening to the downstream opening. The centrifugal flow may increase dispersion of the scent emitted from the surfaces of the fragrance carrier.

The partition may be configured to support the fragrance carrier relative to the fan. The partition may include a plurality of spaced apart annular rings coupled with one another by legs extending between the plurality of spaced apart annular rings. The space between the annular rings may allow air propelled by the fan to pass through the partition and into the fragrance carrier. A light source and a light source housing may be provided. The partition may include a central opening configured to receive the light source housing therethrough. The fragrance carrier may include a central opening configured to receive the light source housing therethrough. The light source housing may align the fragrance carrier with the partition when the light source housing extends through the central opening of the partition and through the central opening of the light source housing. In some embodiments, the light source does not act as a heat source to liquefy the fragrance the fragrance carrier.

A shell for housing the fan may be provided. A first end of the shell may have an engagement feature for receiving the partition at the first end of the shell. The light source housing may protrude through the central opening of the partition. An outer surface of the shell may include radially spaced apart ribs projecting outwardly from the shell.

A vessel may be provided that defines an interior volume. The vessel may have an opening and may be configured to receive the shell through the opening of the vessel to position the shell in the interior volume of the vessel. The opening of the vessel may engage with the radially spaced apart ribs of the shell to axially align the vessel with the shell. The vessel may further including a plurality of vents through the vessel to allow air to flow out from the interior volume of the vessel. In some embodiments, a plurality of alternatively selectable vessels may be provided where each of the plurality of vessels have alternative configurations and designs. Each of the plurality of vessels may include an opening configured to receive the shell through the opening to position the shell in the interior volume of the vessel.

In some embodiments, a detachable power cord may be provided. The first end may be configured to detachably couple with a standard outlet (e.g., 12 v outlet, USB outlet, or the like) and a second end configured to detachably couple with the fan.

In some embodiments, the fragrance delivery system does not include a heater for heating the fragrance carrier. Optionally, the fragrance delivery system does not include a light source. A portable battery may be provided to power the fan. Optionally, the portable battery only powers the fan and may not power any other electronics. In some embodiments, the fragrance delivery system does not include a power cord. Embodiments lacking a heater and/or a light source may be counter-intuitive; however, such embodiments may advantageously last longer on a portable power source and may thus provide extended battery life and a more convenient, moveable, and/or portable fragrance delivery system.

In further aspects of the present invention, a fragrance carrier is provided. The fragrance carrier may be a fragrance disc configured to emit a scent from surfaces of the fragrance disc. While described as a disc, it should be understood that the fragrance carrier may be any other suitable shape and configuration. The fragrance disc may be configured for use with a fragrance delivery system, such as those described above. The fragrance disc may include a first surface and a second surface opposite the first surface. An edge may extend between the first surface and the second surface. A plurality of channels may extend from the first surface of the fragrance carrier to the second surface of the fragrance carrier. Each of the plurality of channels may have side walls that extend from the first surface to the second surface. The plurality of channels may having an upstream opening at the first surface configured to receive air propelled by a fan of the fragrance delivery system and a downstream opening at the second surface of the fragrance carrier. Optionally, the channels may be configured to impart a centrifugal flow on the propelled air as the propelled air flows from the upstream opening to the downstream opening. The centrifugal flow or swirling of the air may increase dispersion of the scent emitted from the surfaces of the fragrance carrier. Optionally, the second surface may be concave and the first surface may be planar.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor it is intended to be used in isolation to determine the scope of the claimed subject matter. The subject matter should be understood by reference to appropriate portions of the entire specification of this patent, any or all drawings and each claim. The invention will be better understood upon reading the following description and examining the figures which accompany it.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

FIGS. 1A-1D illustrate various views of exemplary fragrance delivery systems according to some embodiments of the present invention;

FIGS. 4A-4D illustrate various views of further exemplary fragrance carriers according to some embodiments of the present invention;

FIGS. 5A-5B illustrate various views of exemplary fragrance carriers configured to impart a centrifugal air flow on received axial air flow according to some embodiments of the present invention;

DETAILED DESCRIPTION

Figure 1A:
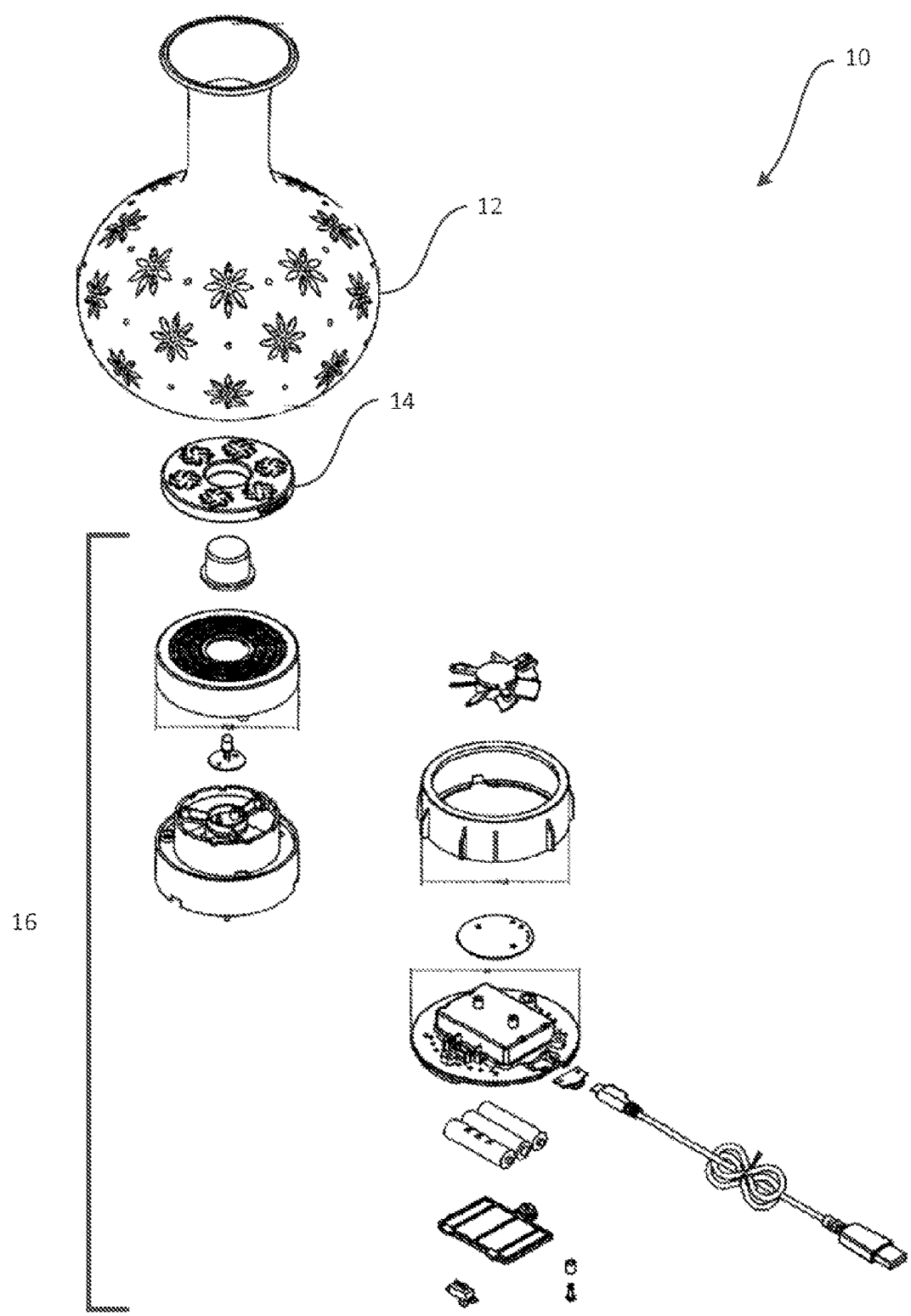
Figure 2A:
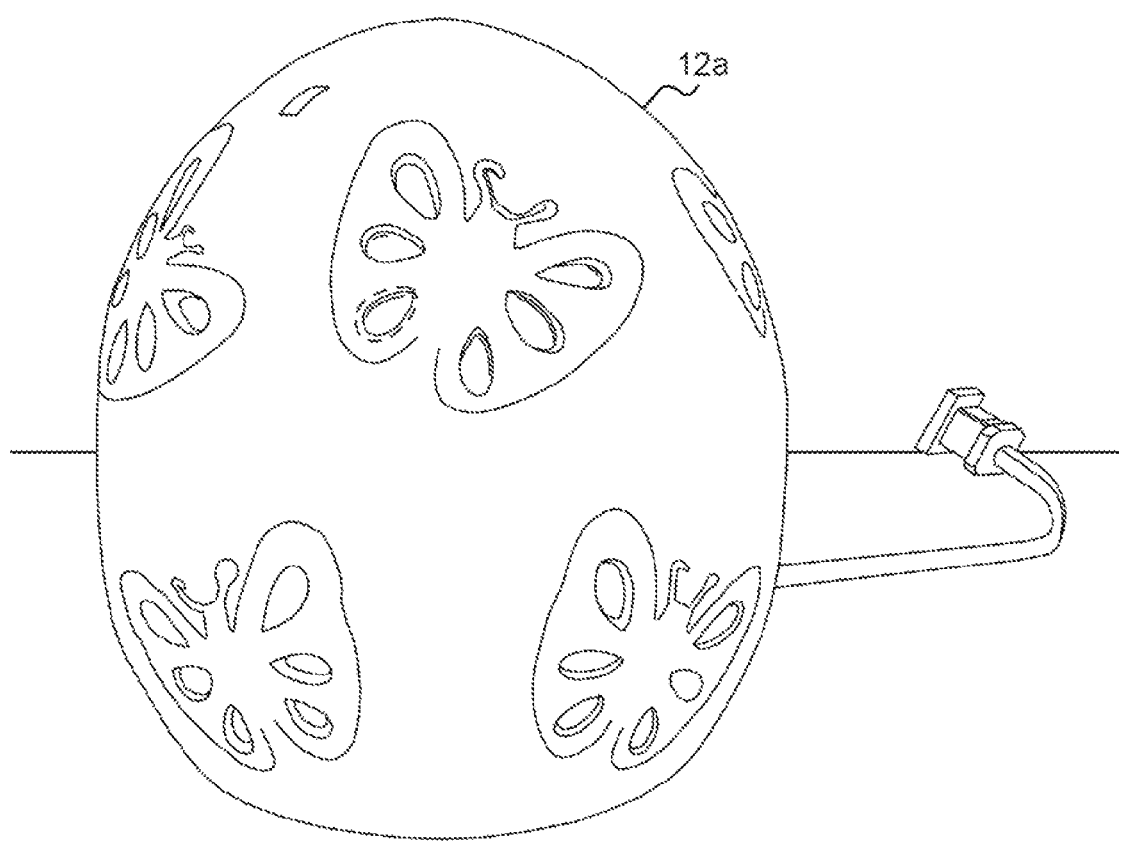
FIGS. 2A-2E illustrate various exemplary vessels that may be used with embodiments of the present invention.
Figure 2B:
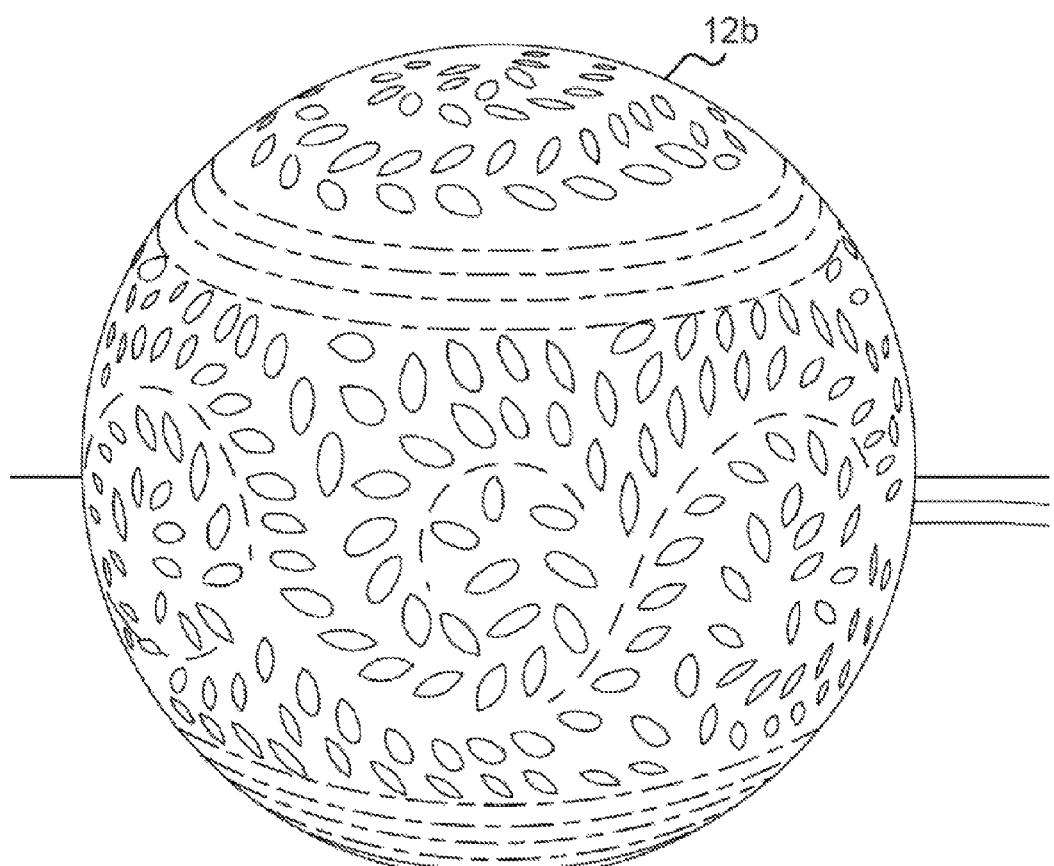
Figure 2C:
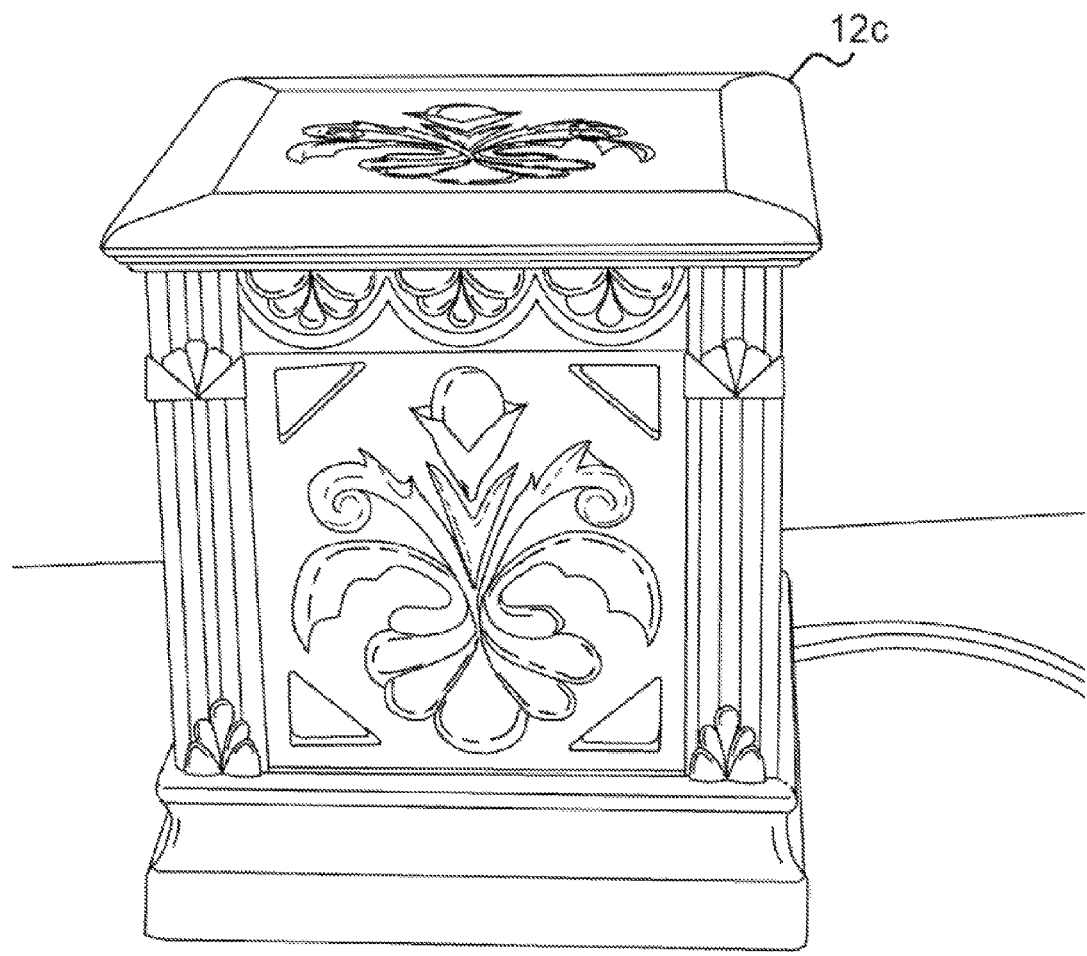
Figure 2D:
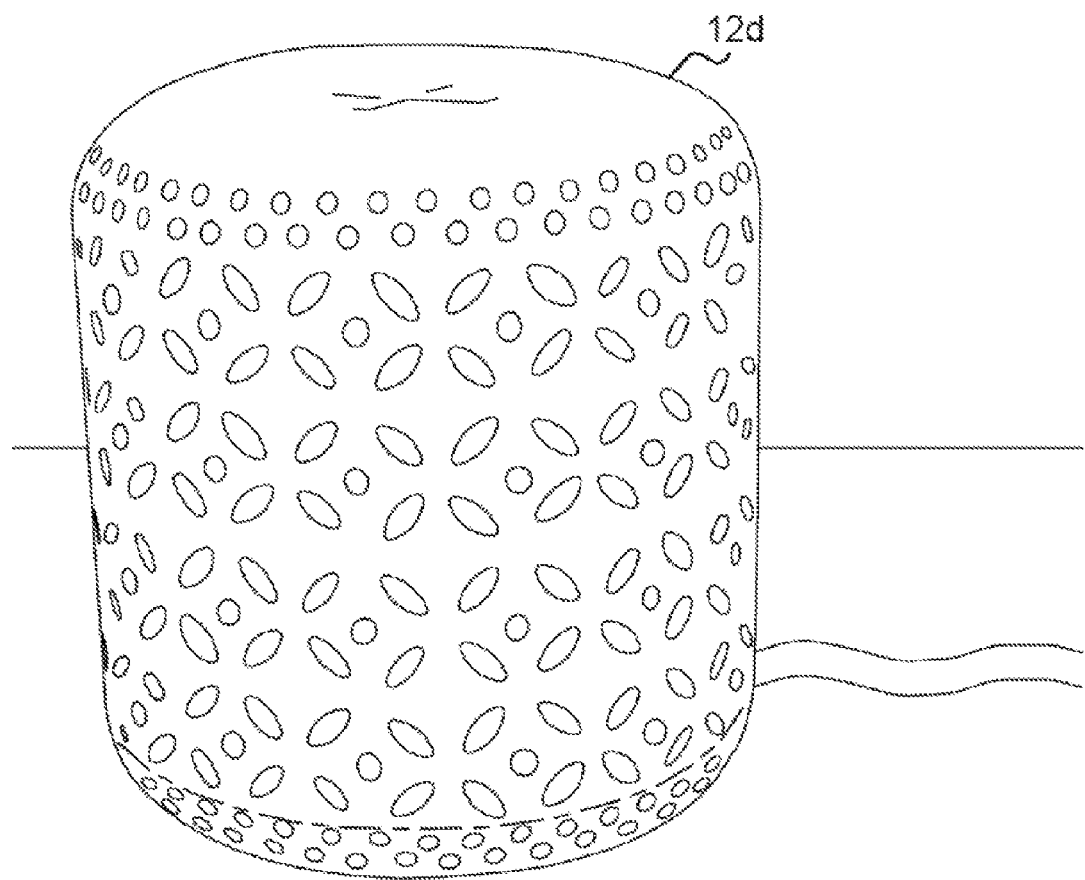
Figure 2E:
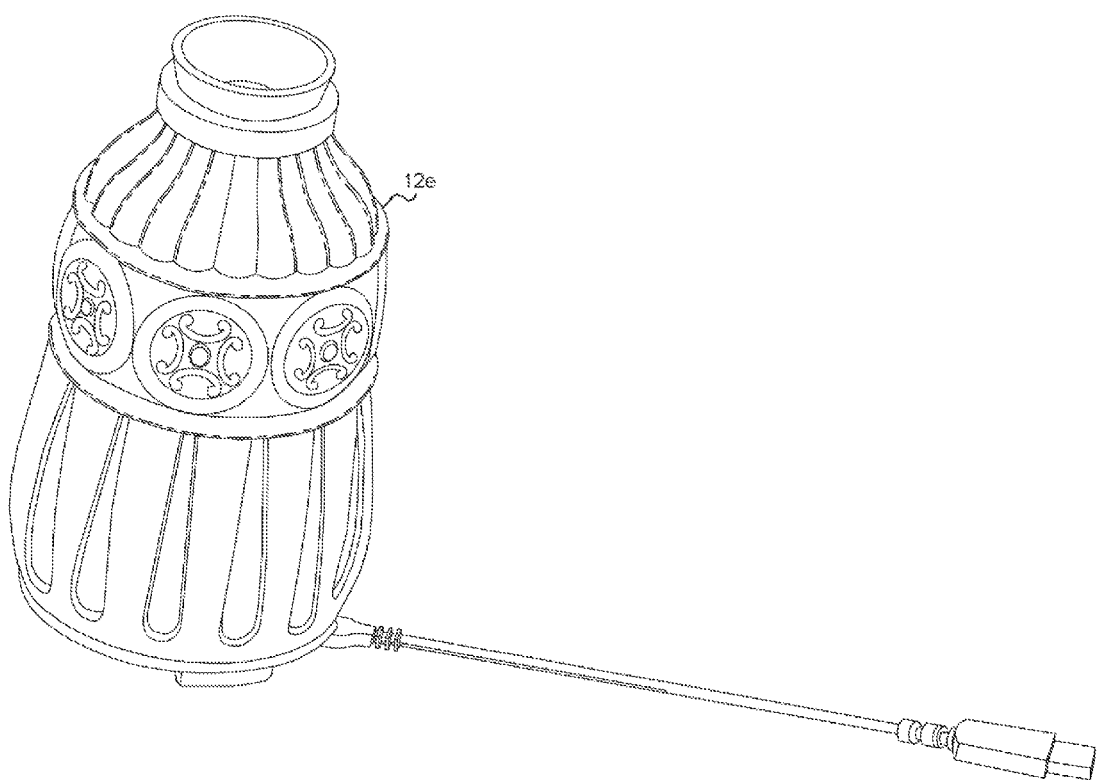

FIGS. 1A-1D illustrate various views of exemplary fragrance delivery systems 10 according to some embodiments of the present invention. FIG. 1A illustrates an exploded view of an exemplary fragrance delivery system 10. FIG. 1B illustrates a side view of the exemplary fragrance delivery system 10. FIG. 1C illustrates a top view of the exemplary fragrance system 10. FIG. 1D illustrates a cross-sectional view of fragrance delivery system 10. Fragrance delivery system 10 includes a vessel 12 configured to house a fragrance delivery carrier 14 and a fragrance delivery device 16. Vessel 12 may define an interior space 18 for housing the fragrance delivery carrier 14 and the fragrance delivery device 16. Vessel 12 may have a narrow neck 20 that extends upwardly to a top opening 22. The top opening 22 may allow vaporizing agents or scents released by the fragrance carrier 14 to move from the interior space 18 of the vessel 12 to the space outside the vessel 12. Additionally, the vessel 12 may include vents or perforations 24 that extend from an interior wall of the vessel 12 to an exterior wall of the vessel 12. The vents or perforations 24 may also allow vaporizing agents or scents released by the fragrance carrier 14 to exit from the interior space 18 of the vessel 12. In some embodiments, the vents or perforations 24 may also provide a decorative pattern on vessel 12. For example, as illustrated in FIGS. 1A-1D, the vents 24 may be configured to resemble flowers on the surface of the vessel 12. The vents 24 may be placed symmetrically about the vessel 12 to provide a decorative appearance for vessel 12. Vessel 12 may further include a bottom opening 26 opposite the top opening 22 for receiving the fragrance delivery carrier 14 and the delivery device 16. The side walls of the bottom opening 26 may be configured to couple with the fragrance delivery device 16 to provide releasable engagement between the vessel and the fragrance delivery device 16. The releasable engagement may allow users to interchange fragrance carriers 14 (e.g., when a fragrance carrier is used up, to change the type of fragrance released, or the like). Additionally, this may be beneficial for users who want to switch and interchange between alternative vessels 12 to provide alternative appearances for fragrance delivery system 12. For example, FIGS. 2A-2E illustrate various exemplary vessels 12a-12e that may be used with embodiments of the present invention. Each vessel 12a-12e may include a bottom opening 26 for releasably engaging with the fragrance delivery device 16. The vessels 12a-12e may be decorative and may be made from ceramic, metal, wood, resin or the like.

Figure 3:
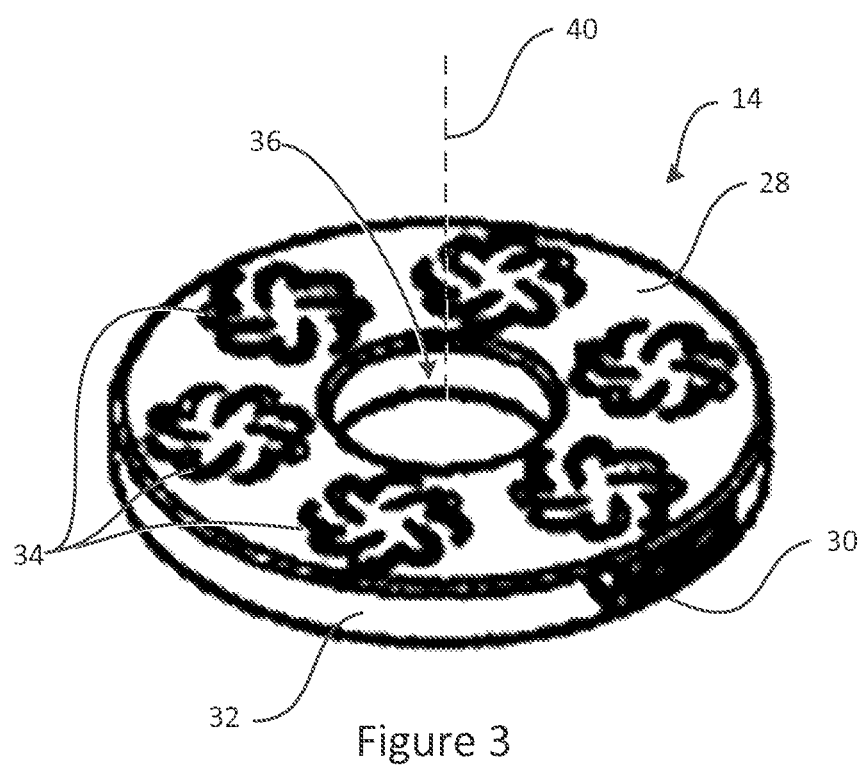
FIG. 3 illustrates exemplary fragrance carriers according to some embodiments of the present invention.

FIG. 3 illustrates exemplary fragrance carriers 14 according to some embodiments of the present invention. The fragrance carrier 14 includes a top surface 28, a bottom surface 30 and an edge 32 extending between the top surface 28 and the bottom surface 30. The fragrance carrier 14 may include a plurality of channels 34 that extend between the top surface 28 and the bottom surface 30. The fragrance carrier 14 optionally may further include a central opening 36 about central axis 40.

In some embodiments, the top surface 28 may be generally flat and bottom surface 30 may be generally flat. In alternative embodiments, the top surface 28 may be convex or domed.

The channels 34 may allow a fan or a blower to blow air around or through the carrier 14 to carry the fragrance a distance from the carrier 14. The top openings of the channels 34 may provide a decorative appearance. For example, the top openings of the channels 34 provide a floral pattern on the top surface of the carrier 14. The floral pattern may be reproduced at radially spaced apart locations of the fragrance carrier 14. In some embodiments, the carrier 14 may have green color, red color, yellow color, or any other color or combinations thereof.

The central opening 36 about central axis 40 of carrier 14 may be configured to cooperate with the fragrance delivery device 16. In some embodiments, the cooperation between the central opening 36 and the fragrance delivery device 16 may preferentially align the fragrance carrier 14 with the fragrance delivery device 16, as will be discussed and illustrated further below.

FIGS. 4A-4D illustrate various views of exemplary fragrance carriers 114 according to some embodiments of the present invention. The fragrance carrier 114, while illustrated as a disc, may take any other configuration, such as a cone, or a dome or the like. Fragrance carrier 114 may include a top surface 128, a bottom surface 130 opposite the top surface 128 and an edge 132 extending between the top surface 128 and the bottom surface 130. The fragrance carrier 114 may include a plurality of channels 134 that extend between the top surface 128 and the bottom surface 130. The fragrance carrier 114 optionally may further include a central opening 136 about central axis 140.

In some embodiments, the top surface 128 may be generally convex and bottom surface 130 may be generally flat. In alternative embodiments, the top surface 128 may also be flat.

The channels 134 may allow a fan or a blower to blow air around or through the carrier 114 to carry the fragrance a distance from the carrier 114. The plurality of channels 134 may have hexagonal cross-sections and may be distributed throughout the fragrance carrier 114 to provide a honeycomb configuration. In some embodiments, the such channels may be holes or tunnels through the carrier having round, oval, triangular, square, octagonal, or other cross sections. The side walls 138 of the channels 134 may be perpendicular with the bottom surface 130 of the carrier 114.

In some embodiments, the side walls 138 of the channels 134 may be at an angle relative to the bottom surface 130 of carrier 114. In some embodiments, the side walls 138 of the channels 134 may be configured to transition axial air flow (parallel to the central axis 140 of the fragrance carrier 114) received at the bottom opening 142 of the channel 134 at the bottom surface 130 to centrifugal air flow (e.g., away from the central axis 140) as the air flow exits the top opening 144 of the channel 134 at the top surface 128. This "swirling" flow imparted by the channels 134 may beneficially increase the dispersion of the fragrance of the fragrance carrier 114.

FIGS. 5A-5B illustrate various views of exemplary fragrance carriers 114 configured to impart a centrifugal air flow on received axial air flow according to some embodiments of the present invention. FIG. 5A illustrates an exemplary carrier 114 with a fan 150 positioned upstream of carrier 114. The fan 150 may include a hub 152 with blades 154 extending from the hub 152. The fan 150 may be configured to rotate about the fan 150 axis 156 to provide axial air flow 160. The axial air flow 160 may enter the bottom openings 142 of the channels 134 along the bottom surface 130 of the carrier 114. The side walls 138 may be configured to transition that axial air flow 160 to centrifugal air flow 162 when the air flow exits from the top opening 144 of channels 134 of the fragrance carrier 114. The swirl flow 162 of the exiting air may advantageously increase the dispersion of the vaporizing agent of the fragrance carrier 114. FIG. 5B illustrates a top view of the exemplary fragrance carrier 114 and the centrifugal/swirling flow 162 being generally perpendicular to the central axis 140 of the fragrance carrier 114 (the channels 134 are not illustrated for clarity purposes only).

While fragrance carrier 114 is discussed above as having channels 134 being configured to transition axial air flow to centrifugal air flow, it should be understood that similar concepts could be applied to fragrance carrier 14. Accordingly, in some embodiments, fragrance carrier 14 may include channels 34 that provide a decorative pattern and may also be configured to impart the swirling flow to improve vaporizing agent/fragrance dispersion.

The fragrance carriers 14, 114 may be fragrance impregnated molded ethylene vinyl acetate (EVA) plastic. The properties of EVA allow it to have absorbed in it, or be impregnated, embedded, or infused with, (collectively referred to herein by use of the term “impregnate” or variations thereof) one or more vaporizing agents, such as for example a fragrance, permitting it to be used as a reservoir for those vaporizing agents. A vaporizing agent is a substance that may be impregnated in a solid carrier, such as for example EVA, but that is also capable of existing in a substantially vaporized and/or aerosolized state at approximately ambient conditions.

Methods for making and using EVA and other polymeric materials and impregnating them with vaporizing agents such as fragrances, odor-neutralizing substances, insecticides and substances having medicinal properties are known in the art. EVA used in the invention may have a molecular weight in the range of 10,000 Daltons to 100,000 Daltons. Vaporizing agents may be impregnated into the EVA at weight percents varying from 10 to 90%, from 20 to 80% from 30 to 70%, from 30 to 60%, and from 30 to 50%.

As an alternative to EVA, other fragrance carriers may be used. For example, in some embodiments, the fragrance carrier may be a fragrance impregnated molded thermoplastic rubber or a fragrance impregnated molded thermoplastic elastomer (TPE). Alternate embodiments of the fragrance disc may be composed of other polymeric materials including but not limited to, polyethylene (high or low density), polypropylene, polyvinyl chloride, polystyrene, polycarbonate, acrylonitrile butadiene styrene (ABS), polyether block amide (PEBA) and polymethylpentene, ethyl vinyl alcohol, polystyrene, acrylic polymers, polycarbonates, polyurethanes, and nylons.

Possible fragrances to be impregnated in the fragrance carrier 14, 114 may be selected from the non-exhaustive list of fragrances including musk oil, civet, castoreum, ambergris, plant perfumes, sandalwood oil, neroli oil, bergamot oil, lemon oil, lavender oil, sage oil, rosemary oil, peppermint oil, eucalyptus oil, menthol, camphor, verbena oil, citronella oil, coconut oil, salvia oil, clove oil, chamomile oil, costus oil, labdanum oil, broom extract, carrot seed extract, jasmine extract, mimosa extract, narcissus extract, olibanum extract, rose extract, acetophenonene and derivatives thereof, dimethylaniline derivatives, naphthaline derivatives, allyl caprate, alpha-amylcinnamic aldehyde, anethole, anisaldehyde, benzyl acetate, benzyl alcohol, benzyl propionate, borneol, cinnamyl acetate, cinnamyl alcohol, citral, citronellal, cumin aldehyde, cyclamen aldehyde, decanol, ethyl butyrate, ethyl caprate, ethyl cinnamate, ethyl vanillin, eugenol, geraniol, exenol, alpha-hexylcinnamic aldehyde, hydroxycitrolnellal, indole, iso-amyl acetate, iso amyl isovalerate, iso-eugenol, linalol, linalyl acetate, p-methylacetophenone, methyl anthranilate, methyl dihydrojasmonate, methyl eugenol, methyl-beta-naphthol ketone, methyl phenyl carbinyl acetate, musk ketol, musk xylol, 2,5,6-nonadienal, gamma-nonalactone, phenyl acetaldehyde dimethyl acetal, beta-phenylethyl alcohol, 3,3,5-trimethylcyclohexanol, gamma-undecalactone, undecenal, vanillin, metofluthrin, and mixtures thereof.

Those of skill in the art will recognize that in constructing the fragrance carrier 14, it may also be desirable to mix the fragrance with hindered amines such as for example, 1-(2-hydroxy-2-methylpropoxy)-4-octadecanoyloxy-2,2,6,6-tetramethylpiperidine; 1-(2-hydroxy-2-methylpropoxy)-4-hydroxy-2,2,6,6-tetramethylpiperidine; and bis(1-octyloxy-2,2,6,6-tetramethyl-4-piperidinyl)sebacate. The foregoing hindered amines may be added to the fragrance at weights of between 0.1% and 2.0% by weight of the EVA (or other carrier), preferably at 0.7% by weight. Further, various antioxidants such as tertiary butylhydroquinone, butylated hydroxyanisole, phenol bisphosphite, and butylated hydroxytoluene may be added to the fragrance at amounts of between 0.015% and 2.5% by weight of the EVA or other, and preferably between 0.2% and 0.5% by weight.

It is contemplated that in alternate embodiments of the invention, the EVA material used in the carrier may also be impregnated with other vaporizing agents such as an insecticide. The insecticide may be selected from the non-exhaustive list of substances including citronella oil, pyrethrum, aluminum phosphide, and magnesium phosphide. Other alternate embodiments of the invention may also utilize a disc impregnated with vaporizing agents having medicinal properties. Such vaporizing agents having medicinal properties may be selected from the non-exhaustive list of preparations including eucalyptus oil, cinnamon oil, eugenol, geranium oil, peppermint oil, lemongrass oil, menthol, camphor, thymol, turpentine oil, I-desoxyephedrine, and bornyl acetate. In other alternate embodiments of the invention, the foregoing substances may be impregnated in the disc in combination with one or more fragrances or alone.

FIGS. 6A-6D illustrate various view of exemplary fragrance delivery device 16. FIG. 6A illustrates a perspective view of exemplary fragrance delivery device 16. FIG. 6B illustrates an exploded view of exemplary fragrance delivery device 16. FIG. 6C illustrates a top view of exemplary fragrance delivery device 16. FIG. 6D illustrates a cross-sectional view of exemplary fragrance delivery device 16. The fragrance delivery device 16 may include a shell or housing 42, disposed about a frame 44. The frame 44 may provide support for shell 42. Additionally, frame 44 may support a fan 46. A base 48 may be provided to couple with a bottom end of the frame 44 and/or the shell 42. A power source 50 may be supported by base 48. The power source 50 may house one or more portable batteries 52. A power cord 54 may couple with the power supply 50. The fragrance delivery device 16 may further include a light source 56 housed in a light source housing 58. In some embodiments, the light source does not act as a heat source to liquefy the fragrance carrier. A partition 60 may be provided to couple with a top end of the frame 44. The partition 60 may be configured with a central opening to allow the light source housing 58 to protrude therethrough. A top surface of the partition 60 may be configured to support the fragrance carrier 14, 114.

In some embodiments, shell 42 may be made of rubber. Shell 42 may generally define a cylinder with an open top end 62 and an open bottom end 64. The inner surface of shell 42 may be configured to be disposed about a bottom portion of the frame 44. The outer surface of shell 42 may include engagement features for coupling the shell 42 with a vessel (e.g., vessel 12, 12a-12e, or the like). The engagement feature may be a plurality of spaced apart fins 66 that extend outwardly from the surface of the shell 42. The fins 66 may be configured to cooperate with the bottom opening of a vessel (e.g., opening 26) in a friction fit manner or the like. In some embodiments, the fins 66 may have a tapered configuration where the fins 66 gradually decrease in height relative to the surface of the shell 42 toward the top of the fins 66. While illustrated as generally cylindrical, it should be understood that other configurations of shell 42 are possible. Further, shell 42 may be made of other materials as desired. Additionally, other types of engagement features may be provided to cooperate with a vessel.

Frame 44 may optionally be used to provide additional support for shell 42. The frame 44 may further include a central support 70. The central support 70 may be configured to support light source 56 and light source housing 58 centrally relative to shell 42 and frame 44. The central support 70 may also couple and support fan 46 within shell frame 44.

Fan 46 may be centrally supported within frame 44 and configured to rotate about a fan axis to provide an axial flow of air in a downstream axial direction (upwards and parallel to axis 47).

Power supply 50 may couple with fan 46 and light source 56 to power each of the components. Batteries 52 may be alkaline batteries, lithium ion batteries or the like. Batteries may be disposable or rechargeable.

Figure 6A:
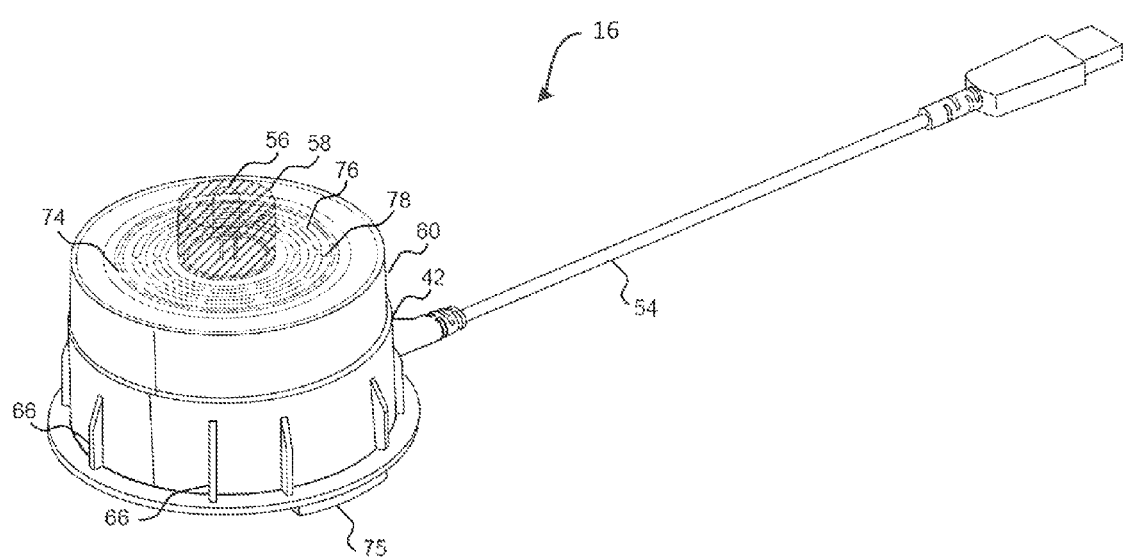
FIG. 6A-6D illustrates exemplary fragrance delivery devices according to some embodiments of the present invention.
Figure 6B:
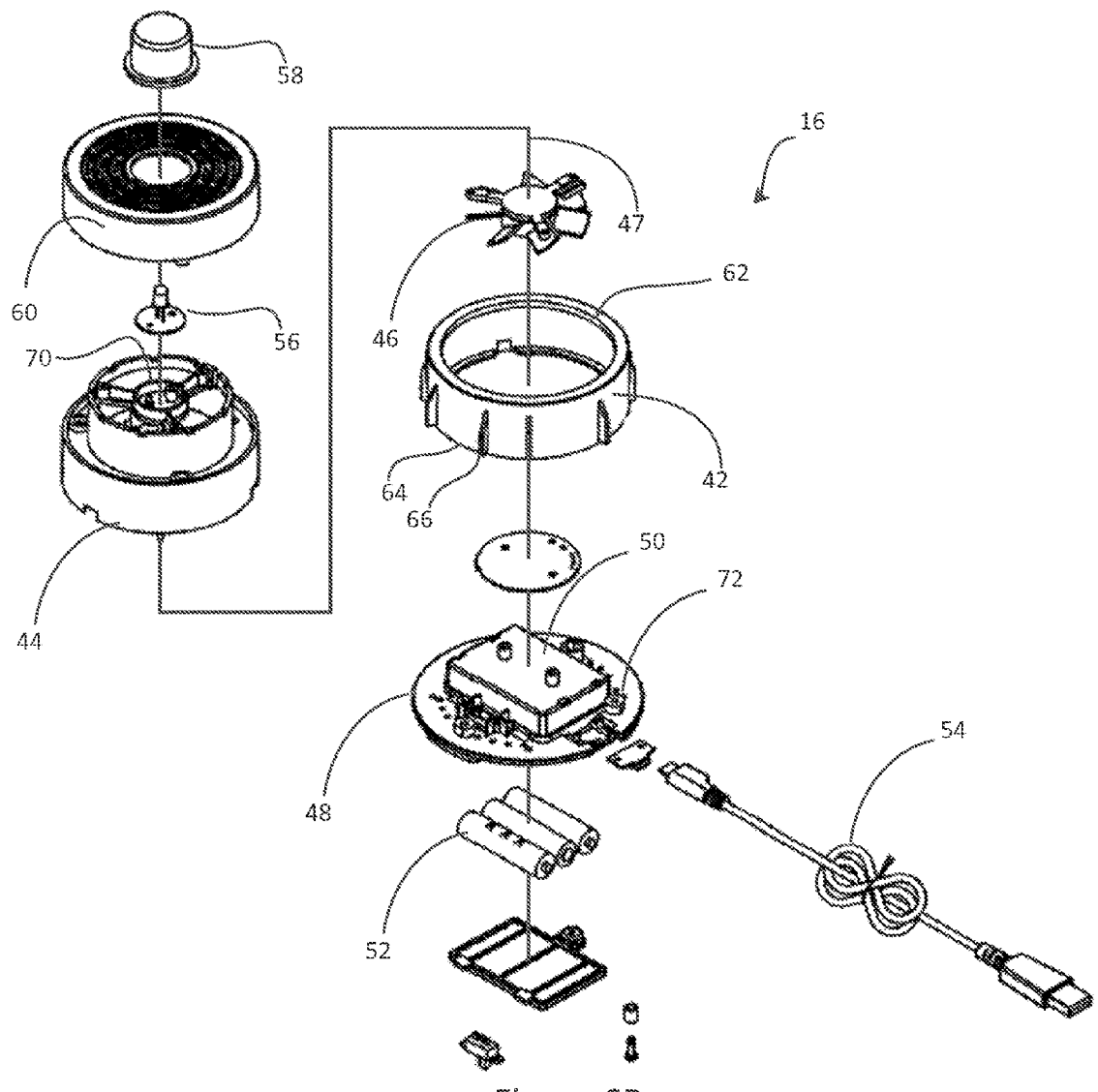

The base 48 may be configured to close off the open end 64 of shell 42 or the bottom end of frame 44. The base 48 may include vents 72. The vents 72 may allow outside air to enter the fragrance delivery device 16 from the bottom of the fragrance delivery device 16. This may provide a continuous supply of air for fan 47 to propel in the downstream direction. In some embodiments, the base 48 further includes feet 75 (FIG. 6A) that may support the base 48 above the support surface to provide clearance for air to be drawn through vents 72 and into shell 42.

In some embodiments, the power supply 50 may be coupled with a power cord 54. The power cord 54 may be an electrical cord with a standard plug for an electrical outlet. In some embodiments, the power cord 54 may be a standard 110 volt cord. In other embodiments, the power cord 54 may be a Universal Serial Bus (USB) to micro-USB or mini-USB plug. In some embodiments, the cord 54 is detachable (during normal user operation) from the power source 50 to provide a more portable fragrance delivery device 16. For example, after recharging a rechargeable battery 52 of the fragrance delivery device 16, a user may detach the cord 54 so as to provide a more compact portable fragrance delivery device 16.

Light source 56 may be one or more light emitting diodes (LED). In some embodiments the light source 56 and/or transparent housing 58 may provide ambient light through the vessel perforations (e.g., perforations 24). Further, light source housing 58 may be configured to fit and project through a central opening of partition 60 and may also project through fragrance carrier 14, 114. The light source housing 58 may thus be used to preferentially align the partition 60 with the fragrance carrier 114. In some embodiments, the light source housing 58 may releasably engage with a fragrance carrier (e.g., fragrance carrier 14, 114). For example, the light source housing 58 may have an outer surface that gradually increases in width along an axis of the light source housing 85 toward a base of the light source housing 58 where the light source housing couples with the partition. The light source housing 58 may define a frusto-conical shape or the like. The gradual increase in width of the outer surface of the light source housing 58 may provide a friction fit engagement between the outer surface of the light source housing and a fragrance carrier (e.g., an inner surface of the central opening of a fragrance carrier). In some embodiments, other engagement surfaces may be provided for cooperation between the light source housing 58 and the fragrance carrier (e.g., dovetail engagement surfaces, threaded engagement surfaces, etc.).

Figure 6C:
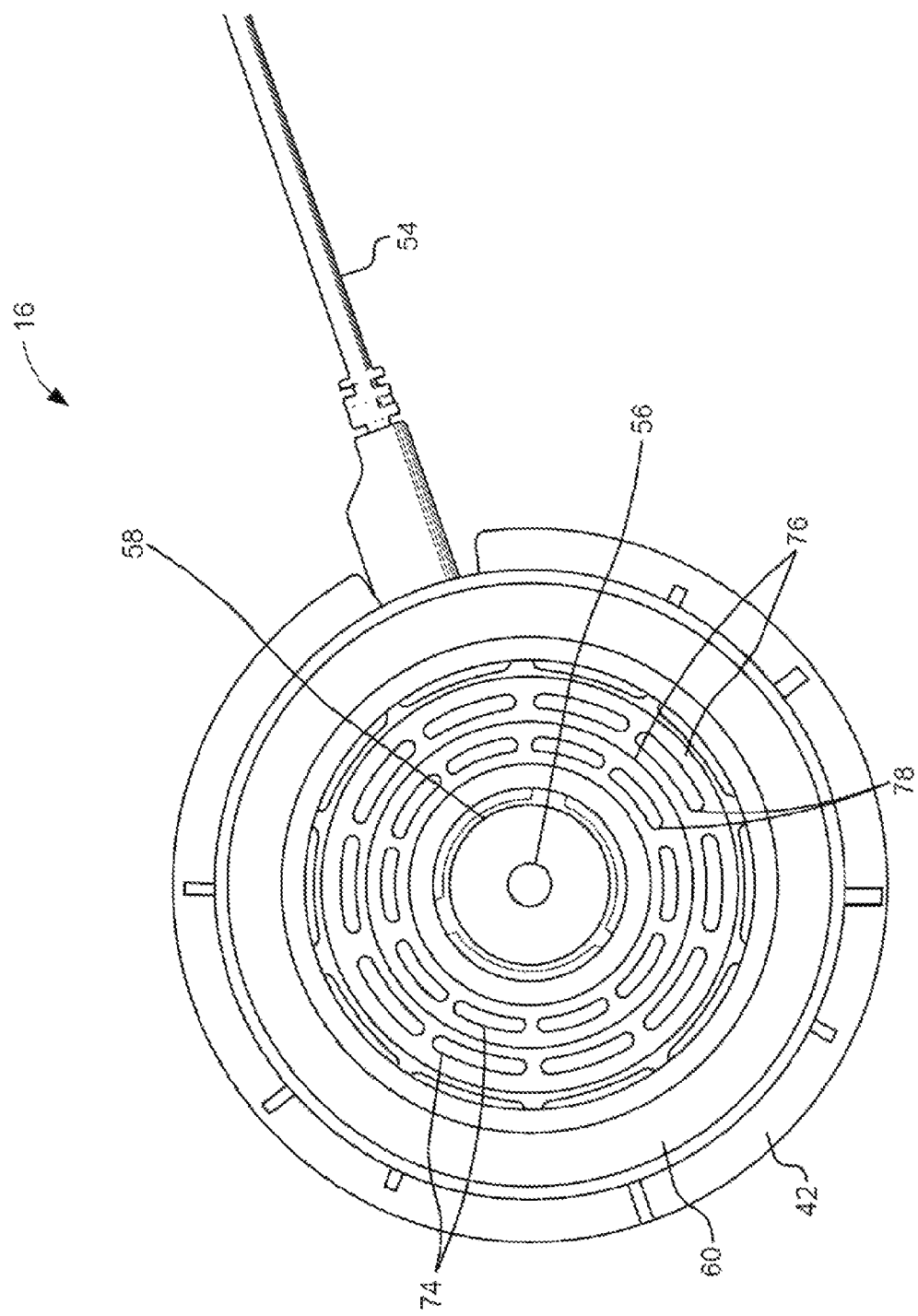
Figure 6D:
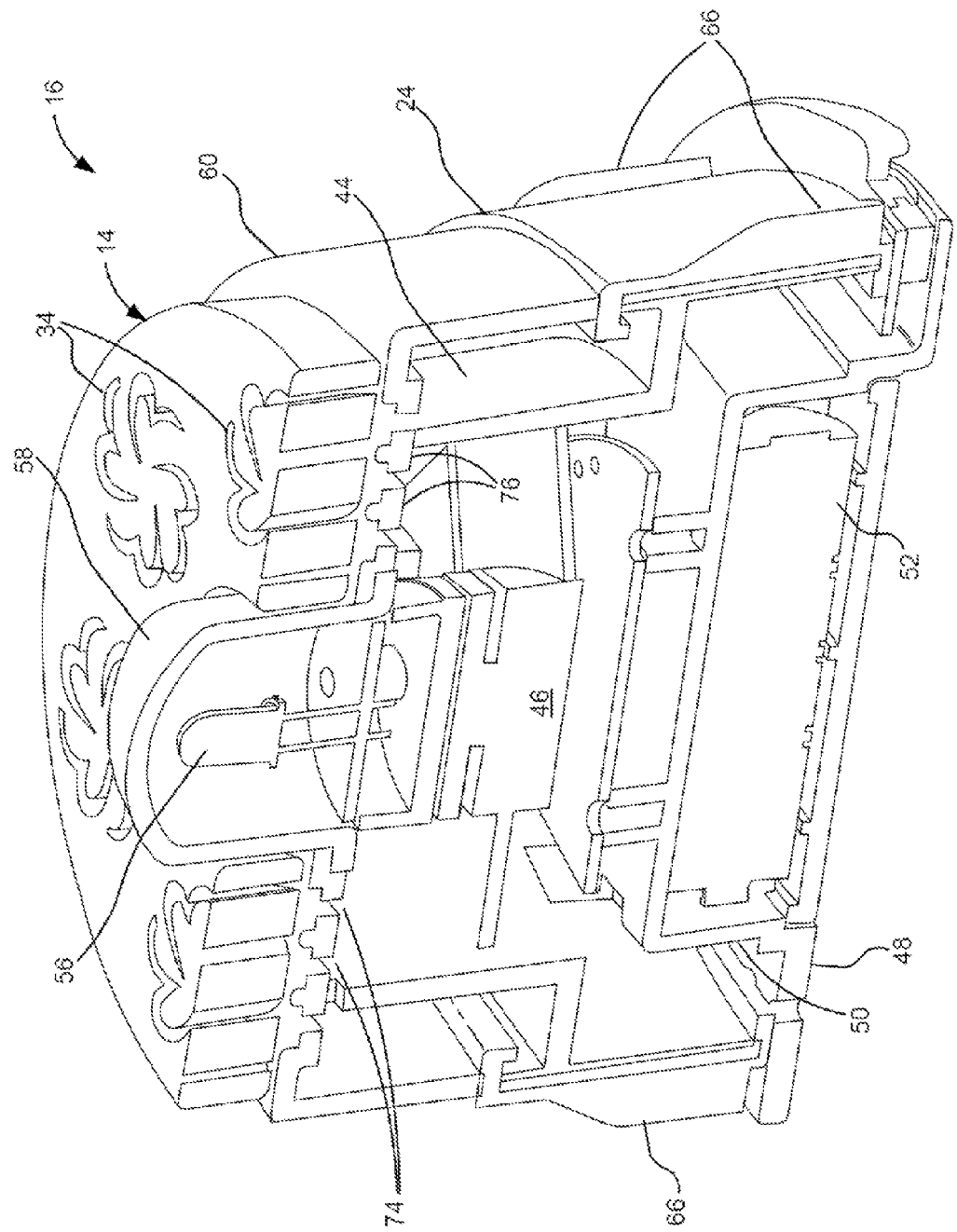

The partition 60 may include vents 74 therethrough. The vents 74 may allow the axial air flow produced by the fan to travel through the partition and into the channels of fragrance carrier 14, 114. In some embodiments, the vents 74 are radial vents generally defined between annular rings 76 of partition 60 as can be more clearly seen in FIG. 6C. The annular rings 76 of partition 60 may be jointed together by legs 78 extending between the annular rings 76. In some embodiments, the light housing 58 may be configured to align the vents 74 with the channels 34 of a fragrance carrier 14 as illustrated in FIG. 6D.

Figure 7A:
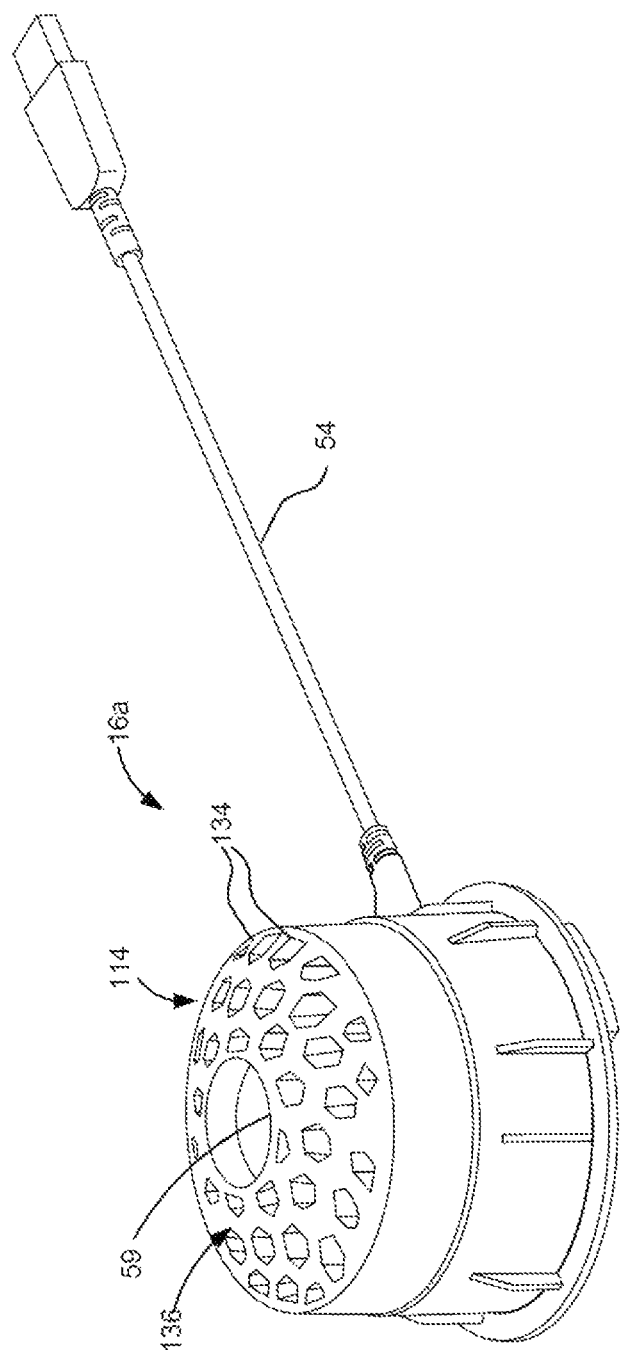
FIGS. 7A-7C illustrate various views of a modified version of the fragrance delivery device of FIGS. 6A-6D and the fragrance carrier of FIGS. 4A-4D according to some embodiments of the present invention.
Figure 7B:
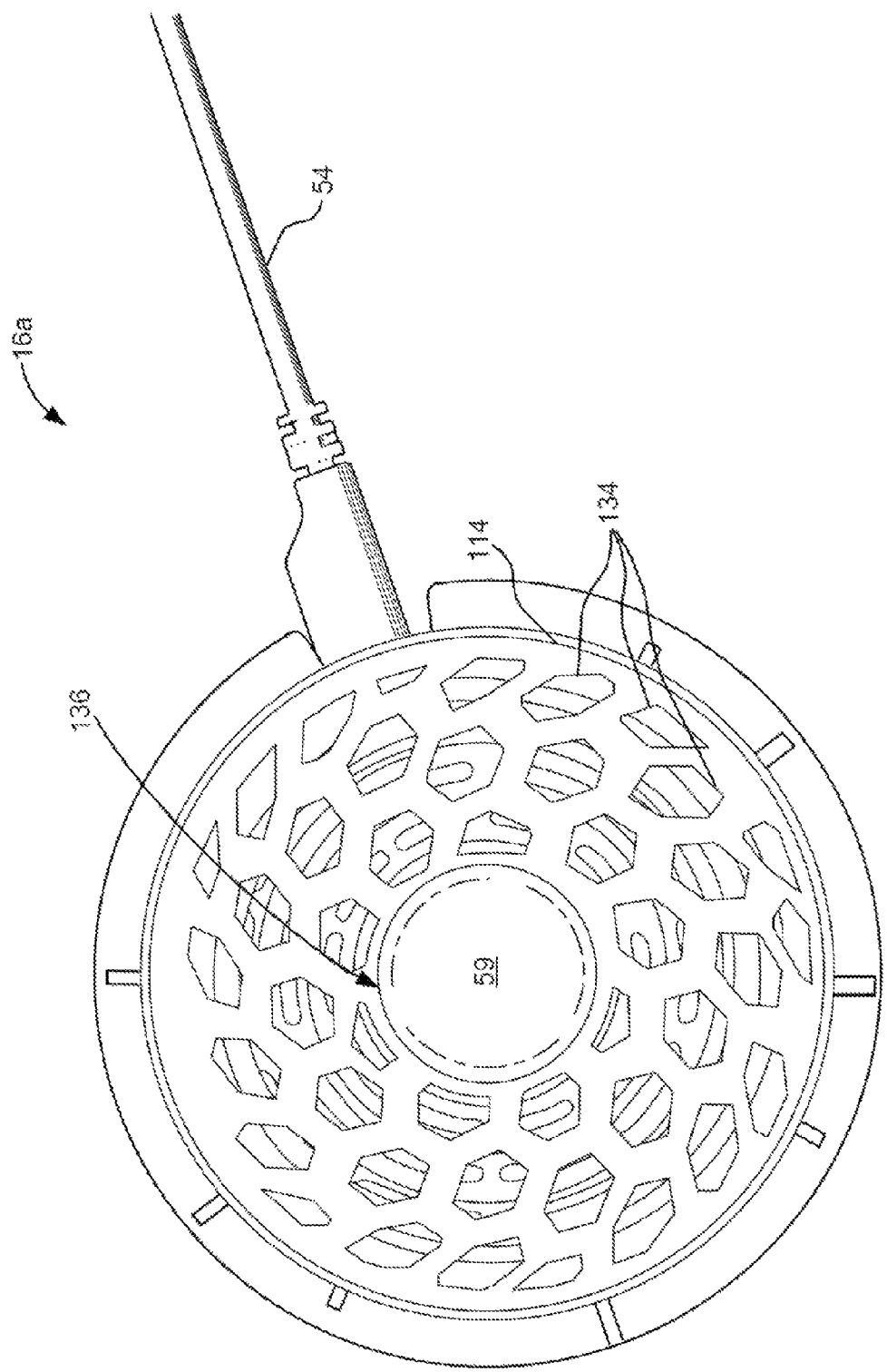
Figure 7C:
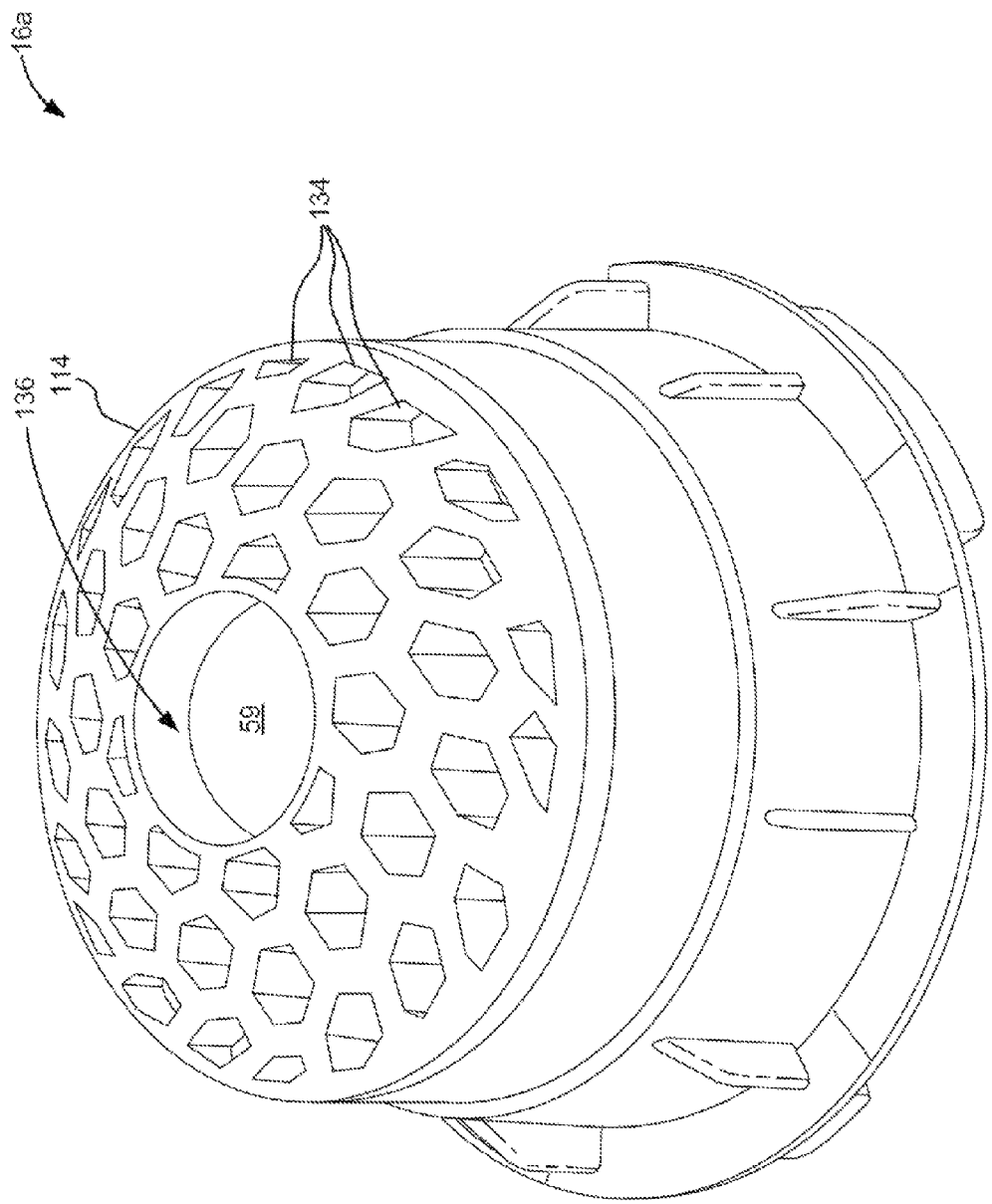

In further embodiments of the invention, the delivery device may not include a light source 56 or light source housing 58. For example, FIGS. 7A-7B illustrate a perspective view and a top view, respectively, of a device 16a that does not include a light source or a light source housing and cooperating with carrier 114. The light source and light source housing may be replaced with a central protrusion 59. Central protrusion 59 may protrude through central opening 136 of carrier 114 to align vents of device 16a with the channels 134 of carrier 114. Embodiments without a light source may be preferable to reduce a power consumption of the device 16a. Additionally it may also be beneficial if the device does not include a heater as a heater may consume a substantial amount of power. By reducing the power consumption of a device 16a, the device 16a may be used for longer periods of time on battery power and without being plugged in. FIG. 7C illustrates device 16a in a portable configuration (e.g., for use outdoors or the like) with the power cord 54 unplugged.

Figure 8:
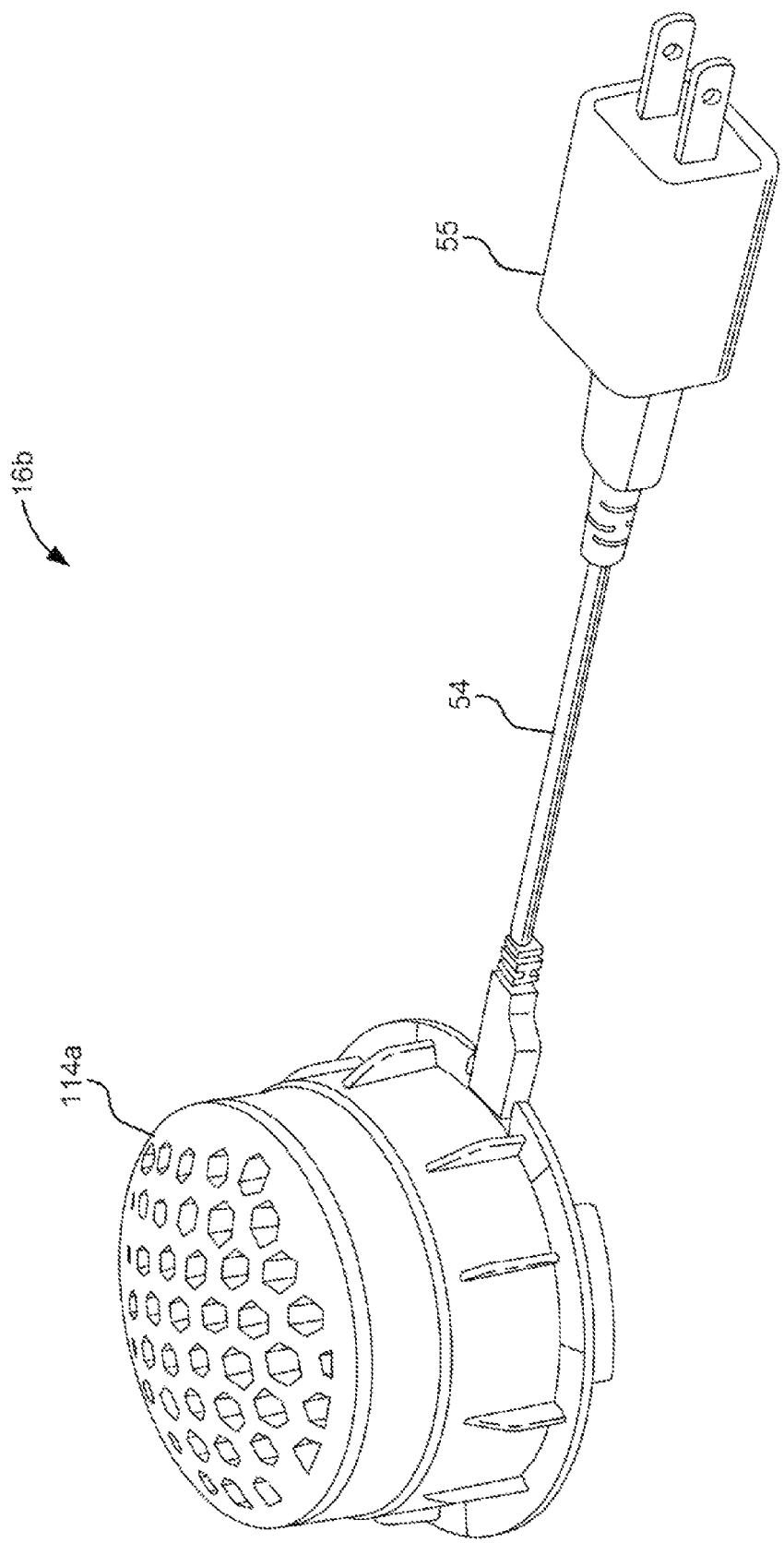
FIG. 8 illustrates another modified version of the fragrance delivery device of FIGS. 6A-6D according to some embodiments of the present invention.

In further embodiments of the invention the delivery device may not include a central protrusion or a light source housing and the fragrance carrier may not include a central opening. For example, FIG. 8 illustrates device 16b that does not include a central protrusion 59 or a light source 56 or light source housing 58. Additionally, carrier 114a does not include a central opening 136. Embodiments without a central opening 136 may be beneficial to provide a larger volume and/or surface area for fragrance carrier 114a. Accordingly, the usable life of fragrance carrier 114a may be increased relative to fragrance carrier 114. Device 16b may further include a USB to wall outlet adaptor 55 such that the device 16b may be charged or powered by a USB port and/or a standard electrical outlet.

Figure 9B:
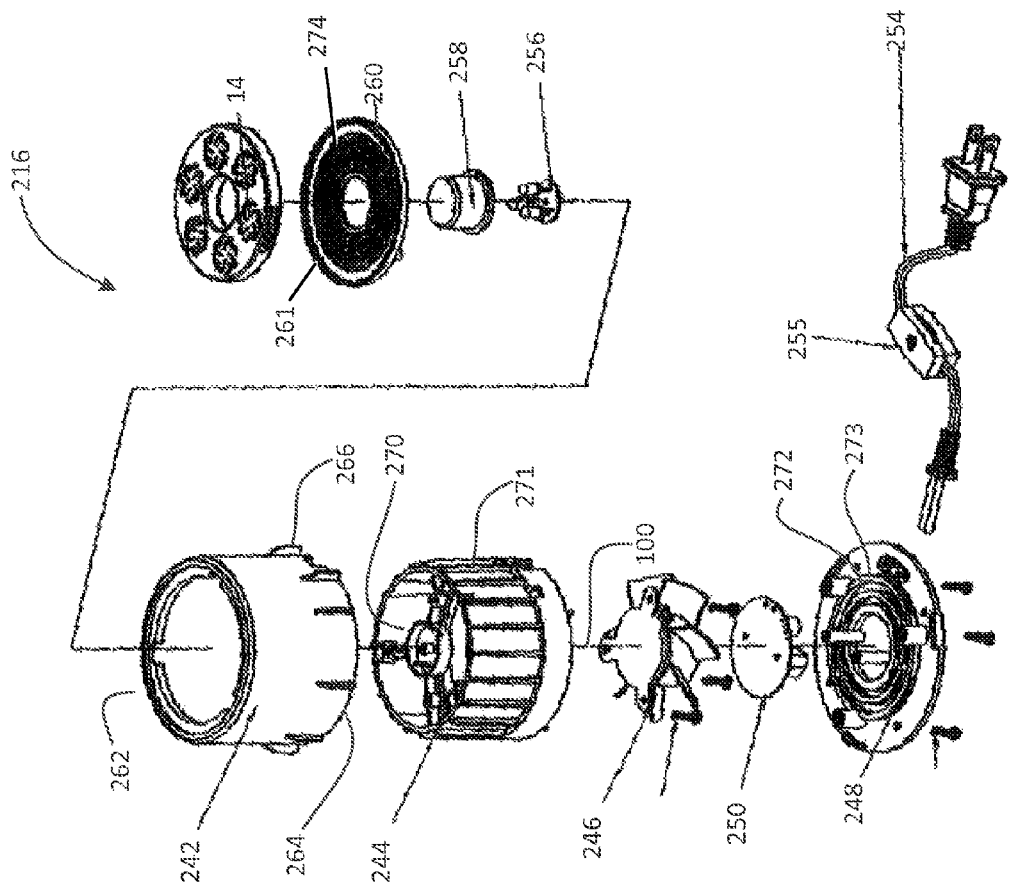
FIGS. 9A-9B illustrate further fragrance delivery devices according to some embodiments of the present invention.
Figure 9A:
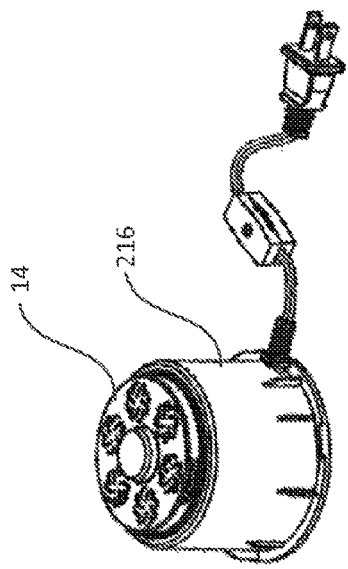

FIGS. 9A-9B illustrate various views of exemplary fragrance carriers 14 and further fragrance delivery devices 216 according to some embodiments of the present invention. FIG. 9A illustrates a perspective view of an assembled fragrance delivery device 216 and a fragrance carrier 14. FIG. 9B illustrates an exploded view of the fragrance delivery device 216 and the fragrance carrier 14. The fragrance delivery device 216 may be similar to fragrance delivery device 16. For example, fragrance delivery device 216 may include a shell or housing 242, disposed about a frame 244. The frame 244 may provide support for shell 242. Additionally, frame 244 may support a fan 246. A base 248 may be provided to couple with a bottom end of the frame 244 and/or the shell 242. A power source 250 may be supported by base 248. A power cord 254 may couple with the power supply 250. An in-line power cord switch 255 may be provided along the power cord 254. The fragrance delivery device 216 may further include a light source 256 housed in a light source housing 258. A partition 260 may be provided to couple with a top end of the shell 242. The partition 260 may be configured with a central opening to allow the light source housing 258 to protrude therethrough. A top surface of the partition 260 may be configured to support the fragrance carrier 14 (or fragrance carrier 114 or the like).

Shell 242 may generally define a cylinder with an open top end 262 and an open bottom end 264. The inner surface of shell 242 may be configured to be disposed about an outer surface of frame 244 to cover substantially all of frame 244. The outer surface of shell 242 may include engagement features 266 similar to that of shell 42 for coupling the shell 242 with a vessel (e.g., vessel 12, 12a-12e, or the like).

Frame 244 may optionally be used to provide additional support for shell 242. The frame 244 may further include a central support 270. The central support 270 may be configured to support light source 256 and light source housing 258 centrally relative to shell 242 and frame 244. The central support 270 may also couple and support fan 246 within shell 242 and frame 244. Frame 244 may include a plurality of vertically oriented ribs 271. The vertically oriented ribs 271 may be configured to couple with an inner surface of shell 242.

The base 248 may be configured to close off the open end 264 of shell 242 or the bottom end of frame 244. The base 248 may include vents 272. The vents 272 may allow outside air to enter the fragrance delivery device 216 from the bottom of the fragrance delivery device 216. The vents 272 may be defined by spaces between a plurality of annular rings 273. This may provide a continuous supply of air for fan 247 to propel in the downstream direction. Accordingly, the housing or shell may define a flow path with an inlet and an outlet. The inlet may be provided by the vents in the base 248 and the outlet may be provided by the vents in the partition. In some embodiments, the base 248 further includes feet (not shown) that may support the base 248 above the support surface to provide clearance for air to be drawn through vents 272 and into shell 242.

Light source 256 may be a plurality of light emitting diodes (LED). In some embodiments the light source 256 and/or transparent housing 258 may provide ambient light through the vessel perforations (e.g., perforations 24).

Partition 260 may further include a raised lip 261 positioned about the perimeter of the partition 260 to help secure the fragrance carrier 14 on the top surface of the partition 260. The partition 260 may include vents 274 therethrough.

The vents 274 may allow the axial air flow produced by the fan to travel through the partition and into the channels of fragrance carrier 14, 114.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A portable fragrance delivery system comprising:
a fan configured to rotate about a fan axis to propel air in a downstream direction from the fan;
a partition disposed downstream from the fan, the partition defining a first surface facing the fan, a second surface opposite the first surface of the partition, and a plurality of openings extending from the first surface of the partition to the second surface of the partition, the openings of the partition configured to allow air propelled by the fan to travel through the partition and to exit from the second surface of the partition in the downstream direction;
a fragrance carrier supported by the second surface of the partition and configured to emit a scent from surfaces of the fragrance carrier, the fragrance carrier comprising a first surface supported by the second surface of the partition and a second surface opposite the first surface of the fragrance carrier, the fragrance carrier further defining a plurality of openings extending from the first surface of the fragrance carrier to the second surface of the fragrance carrier, each of the plurality of openings defined by side walls of the fragrance carrier that extend from the first surface of the fragrance carrier to the second surface of the fragrance carrier,
wherein at least some of the plurality of openings of the partition align with at least some of the plurality of openings of the fragrance carrier such that at least a portion of air propelled by the fan that travels through the partition and that exits from the second surface of the partition will flow through at least some of the openings of the fragrance carrier to propel the scent emitted from the side walls of the fragrance carrier outwardly in the downstream direction from the second side of the fragrance carrier,
wherein the portable fragrance delivery system does not include a heater for heating the fragrance carrier, and
wherein the partition comprises a plurality of spaced apart annular rings coupled with one another by legs extending between the plurality of spaced apart annular rings.

2. The portable fragrance delivery system of claim 1, wherein the portable fragrance delivery system does not include a light source.

3. The portable fragrance delivery system of claim 1, further comprising a portable battery, wherein the portable battery only powers the fan.

4. The portable fragrance delivery system of claim 3, wherein the portable fragrance delivery system does not include a power cord.

5. A fragrance delivery system comprising:
a fan configured to rotate about a fan axis to draw air from an inlet in the upstream direction from the fan and to propel air to an outlet in a downstream direction from the fan along a flow path of the fan;
a partition having a first surface facing the fan, a second surface opposite the first surface of the partition, and a plurality of vents defining the outlet of the fan flow path that extend from the first surface of the partition to the second surface of the partition, the plurality of vents of the partition configured to allow air propelled by the fan to travel through the partition and to exit from the second surface of the partition in the downstream direction;
a protrusion projecting from the partition in a downstream direction, the protrusion having an engagement surface for releaseably engaging with a fragrance carrier; and
a base housing disposed upstream of the fan, the base housing having a first surface facing the fan, a second surface opposite the first surface of the base housing, and a plurality of vents defining the inlet of the fan flow path that extend from the second surface of the base housing to the first surface of the base housing, the plurality of vents of the base housing configured to allow air to be drawn by the fan to travel through the base housing and toward the fan,
wherein the partition comprises a plurality of spaced apart annular rings coupled with one another by legs extending between the plurality of spaced apart annular rings, and
wherein the space between the annular rings defines the plurality of vents that allows air propelled by the fan to pass through the partition.

6. The fragrance delivery system of claim 5, wherein the partition comprises a central opening and a central protrusion projecting from the central opening in a downstream direction, the central protrusion having an engagement surface for releaseably engaging with a fragrance carrier.

7. The fragrance delivery system of claim 6, wherein the central protrusion projecting from the central opening of the partition in the downstream direction has an outer surface with a width that increases toward a base of the central protrusion, wherein the outer surface of the central protrusion is configured to friction fit with a central opening a fragrance carrier.

8. The fragrance delivery system of claim 7, wherein the central protrusion has a frustoconical configuration.

9. The fragrance delivery system of claim 6, wherein the central protrusion comprises a transparent light source housing, and wherein the system further comprises a light source, wherein the light source housing aligns a fragrance carrier with the partition when the light source housing engages with the fragrance carrier.

10. The fragrance delivery system of claim 9, further comprising a shell for housing the fan, a first end of the shell having an engagement feature for receiving the partition at the first end of the shell and wherein an outer surface of the shell includes radially spaced apart ribs projecting outwardly from the shell.

11. The fragrance delivery system of claim 10, further comprising a vessel defining an interior volume and having an opening, the vessel configured to receive the shell through the opening of the vessel to position the shell in the interior volume of the vessel, and wherein the opening of the vessel engages with the radially spaced apart ribs of the shell to axially align the vessel with the shell, the vessel further including a plurality of vents through the vessel to allow air to flow out from the interior volume of the vessel.

12. The fragrance delivery system of claim 5, wherein the fragrance delivery system does not include a heater for heating the fragrance carrier.

13. The fragrance delivery system of claim 5, further comprising a detachable power cord having a first end configured to detachably couple with a standard outlet and a second end configured to detachably couple with the fan.

14. The fragrance delivery system of claim 12, wherein the fragrance delivery system does not include a light source.

15. The fragrance delivery system of claim 14, further comprising a portable battery, wherein the portable battery only powers the fan.

16. The fragrance delivery system of claim 15, wherein the fragrance delivery system does not include a power cord.

* * * * *